United States Patent

Vertesy et al.

[11] Patent Number: 5,519,123
[45] Date of Patent: May 21, 1996

[54] CHELATING AGENTS, THEIR PREPARATION FROM THE ANTIBIOTICS SALMYCIN A,B,C, OR D, AND THEIR USE

[75] Inventors: László Vertesy, Eppstein; Werner Aretz, Königstein; Hans-Wolfram Fehlhaber, Idstein, all of Germany

[73] Assignee: Hoechst Aktiengesellschaft, Frankfurt am Main, Germany

[21] Appl. No.: 286,452

[22] Filed: Aug. 5, 1994

[30] Foreign Application Priority Data

Aug. 13, 1993 [DE] Germany .................. 43 27 226.6

[51] Int. Cl.$^6$ .................. C07H 13/04; A61K 31/70
[52] U.S. Cl. .................. 536/13
[58] Field of Search .................. 536/13; 514/28

[56] References Cited

PUBLICATIONS

Bergeron et al., "The Total Synthesis of Desferrioxamines E and G," Tetrahedron, 46, 5881–5888 (1990).

"Stoffwechselprodukte von Mikroorganismen", P. Huber et. al., Helvetica Chimica Acta, 69:236–245 (1986).

"Sysnthesis of the Metabolite—Hydroxy–Desferrioxamine B", Barbara Roggo et. al., The Journal of Antibiotics, 46(2):294–299 (Feb. 1993).

Primary Examiner—Nathan M. Nutter
Attorney, Agent, or Firm—Finnegan, Henderson, Farabow, Garrett & Dunner

[57] ABSTRACT

The novel substances nordanoxamine and desferrinordanoxamine, and desferrisalmycin A, B, C and D, as well as the known substances danoxamine and desferridanoxamine, are prepared from the antibiotics salmycin A, B, C and D, which are obtained by fermentation. These substances are used as chelating agents and pharmaceuticals.

8 Claims, No Drawings

CHELATING AGENTS, THEIR PREPARATION FROM THE ANTIBIOTICS SALMYCIN A,B,C, OR D, AND THEIR USE

The present invention relates to chelating agents, their preparation from the salmycins A, B, C or D, and their use as pharmaceuticals.

Salmycins can be obtained by fermentation using the microorganism Streptomyces violaceus 37290 (DSM 8286) (Patent Application: L. Vertesy et al., "Antibiotics, called Salmycin A, B and C, a process for their preparation and their use as a pharmaceutical", Hoechst AG (cf. EP 93 118 511.9 as well)). The salmycins are iron-containing antibiotics, so-called sideromycins, which comprise a chelate component and an amino-disaccharide component. The presumed structures of salmycin A to D are represented by formula I:

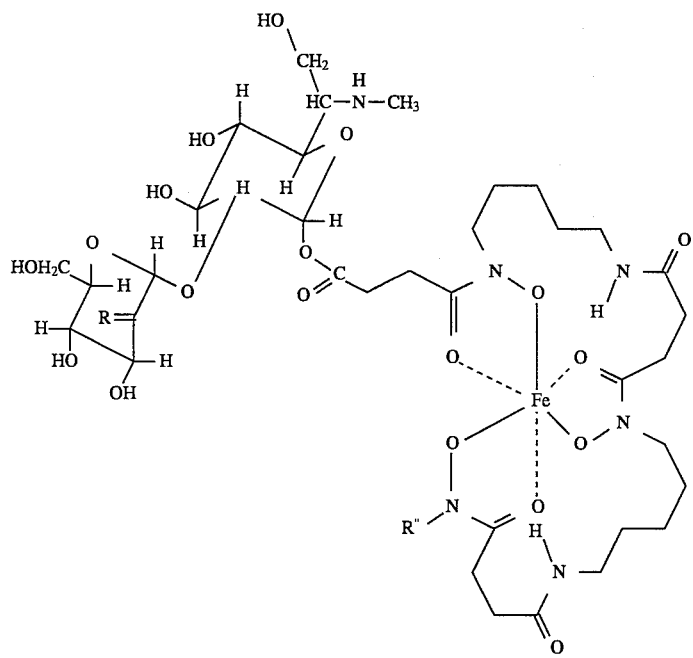

Salmycin A: R=NOH, R"=—$(CH_2)_5$—OH
Salmycin B: R=O, R"=—$(CH_2)_5$—OH
Salmycin C: R=O, R"=—$(CH_2)_4$—OH
Salmycin D: R=NOH, R"=—$(CH_2)_4$—OH The iron chelate danoxamine (P. Huber et al., Helv. Chim. Acta 69 (1986) 236–245), which is already known, is prepared from salmycin A and B by hydrolysis. Danoxamine has the empirical formula $C_{27}H_{46}FeN_5O_{11}$ and a molecular weight of 672 g/mol. Formula II shows the structure of danoxamine.

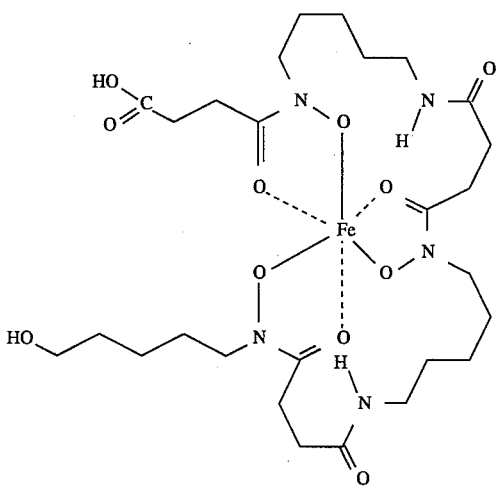

It has now been found, surprisingly, that the iron chelate nordanoxamine, which has not previously been described, can be obtained from salmycins C and D.

The invention consequently relates to the compound, termed nordanoxamine, having the empirical formula $C_{26}H_{44}FeN_5O_{11}$ and a molecular weight of 658 g/mol, as well as to its iron-free form, termed desferrinordanoxamine, having the empirical formula $C_{26}H_{47}N_5O_{11}$ and a molecular weight of 605 g/mol. Nordanoxamine has the following structure

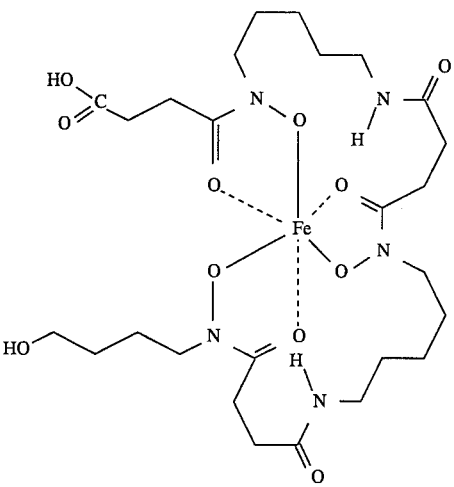

II'

The present invention also relates to the iron-free compounds desferrisalmycin A, B, C and D.

The present invention relates furthermore to a process for preparing danoxamine and nordanoxamine by hydrolysing salmycin A, B, C or D.

The salmycins preferably derive from a fermentation process using the microorganism Streptomyces violaceus (DSM No. 8286), as described in the patent application of L. Vertesy et al., "Antibiotics, called Salmycin A, B and C, a process for their preparation and their use as a pharmaceutical" and in EP 93 118 511.0. The hydrolysis of the salmycins should be carried out under mild conditions, and can be effected at room temperature in dilute alkaline solution, e.g. ammonium hydroxide solution, preferably at pH 9.5. In general, the hydrolysis of the salmycins is largely complete after 2 hours. It is advantageous to neutralize the reaction solution for the subsequent working-up. The danoxamine and nordanoxamine contained in the solution can be separated off and purified using chromatographic methods, in particular reversed-phase chromatography, e.g. using $C_{18}$ silica gel as the partition support and a mixture of water and acetonitrile as the mobile phase, preferably using a concentration gradient of 0–15% by volume of acetonitrile.

The preparation of danoxamine, nordanoxamine and their iron-free forms from salmycins A, B, C and D is particularly advantageous compared with known processes since the products are available in larger quantities and they can be obtained in a particularly economical manner. Previously, it was not possible to use danoxamine on an industrial scale since it was previously only possible to prepare it in very small quantities from danomycin, which is difficult to obtain. In addition to this, the products according to the invention are obtained in high purity.

The present invention furthermore relates to a process for preparing desferridanoxamine from salmycin A and/or B and desferrinordanoxamine from salmycin C and/or D by hydrolysis and treatment with other sequestering agents or by reduction of the bound $Fe^{3+}$ ion. The compounds obtained in this way are very active in binding free $Fe^{3+}$ and $Al^{3+}$ ions. Desferridanoxamine, which has already been described (P. Huber et al., Helv. Chim. Acta 69 (1986) 236–245), and des ferrinordanoxamine, which has not previously been known and which has the empirical formula $C_{26}H_{47}N_5O_{11}$ and a molecular weight of 605 g/tool, are obtained in this manner.

In preparing the iron-free forms desferridanoxamine or desferrinordanoxamine there is no need to isolate danoxamine and nordanoxamine. Once hydrolysis has taken place, the reaction mixture can be treated directly, in order to remove the bound iron, with a sequestering agent, an iron-binding reagent or a reducing agent, or be subjected to cathodic reduction. All the customary complexing agents which are able to bind iron(III) ions, such as, for example, ethylene diaminetetraacetic acid or 8-hydroxyquinoline, are suitable for use as sequestering agents. Hydrogen sulfide is an example of an iron binding reagent. Sodium thiosulfate, sodium sulfite or hydroquinone, for example, can be used as reducing agents. Cathodic reduction is preferably effected in a divided cell having a cathode made of platinum, nickel, steel, graphite, glassy carbon or other customary cathode materials.

The present invention furthermore relates to a process for preparing desferrisalmycin A, desferrisalmycin B, desferrisalmycin C and desferrisalmycin D by treating salmycin A, B, C or D with sequestering or iron-binding reagents or by reducing the bound $Fe^{3+}$ ion. The preparation conditions which are preferred have already been described above for the preparation of desferridanoxamine and desferrinordanoxamine.

The iron-free compounds desferridanoxamine, desferrinordanoxamine, desferrisalmycin A, desferrisalmycin B, desferrisalmycin C and desferrisalmycin D can be used as agents which thelate triply charged metal ions, in particular the metal ions $Fe^{3+}$ and $Al^{3+}$. Because of these properties, there are a variety of industrial uses for these compounds. The compounds are of particular importance in pharmaceutics. When administered in vivo, these chelating agents take up $Fe^{3+}$ and $Al^{3+}$ in the organism and thereby promote the excretion of these ions. For this reason, they represent valuable pharmaceuticals which can be successfully employed, in particular, in hemochromatosis, an iron-storage disorder characterized by excessively high $Fe^{3+}$ concentrations, or in Alzheimer's disease, characterized by excessively high $Al^{3+}$ concentrations. As compared with desferrioxamine B (see B.E. Roggo and H.H. Peter, J. Antibiotics 46 (1993) 294–299), which is already being marketed as a pharmaceutical (®Desfetal), desferridanoxamine and desferrinordanoxamine do not exhibit any restricted tolerance and are non-toxic, even in high doses. Desferrisalmycin A, B, C and D have similar properties. The present invention also relates, therefore, to the use of desferridanoxamine, desferrinordanoxamine, desferrisalmycin A, B, C and D, and their physiologically tolerated salts, such as, for example, their lithium, sodium, potassium, calcium or ammonium salts, as pharmaceuticals.

The pharmaceuticals according to the invention may contain one or more of the listed chelating agents and one or more carrier or auxiliary substances, such as, for example, fillers, emulsifiers, glidants, flavorants, dyes or buffering substances, and may be administered parenterally in a suitable pharmaceutical form, such as, for example, tablets, capsules, a suspension or a solution.

Examples of carrier substances are tragacanth, lactose, talc, agar-agar, polyglycols, hydrocolloids, ethanol or water. Suspensions or solutions in water, for example, are suitable and preferred for a parenteral administration. It is likewise possible to administer the active substance without additives in a suitable form such as capsules.

EXAMPLES

Example 1: Cultivation of Streptomyces violaceus

Streptomyces violaceus (DSM 8286) is maintained on the following solid nutrient medium:

Starch: 10 g/l
Casein: 1 g/l
Peptone: 1 g/l
Yeast extract: 1 g/l
Malt extract: 10 g/l
$K_2HPO_4$: 0.5 g/l
Agar: 15 g/l The medium is sterilised at 121° C. for 30 minutes, cooled down to 45° C. and used to fill petri dishes. The petri dishes are inoculated with a spore suspension and incubated at 28° C. for 8 days. They are stored at 4° C. 1 $cm^2$ of an incubated plate is used as the inoculum for 500 ml of preculture of the following composition:

Glucose: 15 g/l
Soya bean meal: 15 g/l
Cornsteep, fl. 5 ml/l
$CaCO_3$: 2 g/l
NaCl: 5 g/l
pH 7.2

The incubation takes place at 28° C. for 2 days on a rotary shaker at a shaking frequency of 240 rpm. 25 ml of the preculture are used as the inoculum for a main culture (50 ml/300 ml conical flask) of the following composition:
Soya bean meal: 20 g/l
Mannitol: 20 g/l
pH 7.5

The main culture is incubated at 28° C. and at 240 rpm for 3–4 days. At the end of this time, a biological activity of a 21–23 mm diameter inhibitory halo against Staphylococcus aureus 209 P is observed in a diffusion test.

Example 2: Production of salmycins A, B, C and D in a fermenter

Strain maintenance and precultivation of Streptomyces violaceus (DSM 8286) are carried out in analogy with Example 1. Growth of the main culture takes place in a 12 l fermenter containing 9 l of main culture nutrient solution from Example 1. The inoculum amounts to 1% of the fermenter volume. Incubation is carried out at 28° C. and at 500 rpm for 2–3 days employing an aeration rate of 0.5 l/min. On average, biological activities of a 22–27 mm inhibitory halo are achieved against Staphylococcus aureus 209 P.

Example 3: Isolation of crude salmycin 180 l of filtrate from the cultures obtained in accordance with Example 2 are adjusted to pH 6.8 and loaded onto a column filled with 17 l of an adsorption resin. A styrene/ divinylbenzene copolymer in powder form, such as ®Diaion HP-20 (Mitsubishi Chem. Ind., Japan), is preferably used as the adsorbent. The loaded support material is then washed with desalinated water. The salmycin complex is then eluted with a gradient containing 0–20% by volume of isopropanol. Fractions are collected and examined for antibacterial activity. The salmycin-containing fractions are combined (approximately 30 l in all). In order to remove acidic impurities, the liquid is filtered through an anion-exchange column (e.g. 1 l of diethylaminoethyl Sepharose, such as DEAE-® Sephadex Fast Flow Ion Exchanger from Pharmacia Fine Chemicals AB, Sweden), which has previously been equilibrated with ammonium acetate solution, pH 7.0. The solution is subsequently concentrated by ultrafiltration using a semipermeable and permselective membrane, such as, for example, a "®Nadir UF-CA-1" membrane (Hoechst; Frankfurt, Germany), and freeze-dried. This results in 38 g of the crude salmycin product.

Example 4: Preliminary fractionation of the crude product mixture 35 g of the crude product mixture obtained in accordance with Example 3 are dissolved in 500 ml of distilled water and loaded onto a column of 3.5 l capacity (11.3 cm inner diameter, 36 cm height), which is packed with an adsorbent based on styrene/divinylbenzene copolymer, such as, for example, "®MCI GEL CHP 20 P" (Mitsubishi Kasei Corp., Tokyo, Japan). Washing with water then takes place, followed by elution using a water/10% by volume isopropanol in water gradient. Fractions are taken by the liter. Fractions containing salmycin B and C, and fractions which mainly contain salmycin A and D, are obtained. Concentration in vacuo, and freeze-drying, yield 3.2 g of a crude mixture of salmycin B and C and 1.4 g of crude salmycin A and D.

Example 5: Purification of salmycin B and C

The crude mixture of salmycin B and C obtained in accordance with Example 4 is passed through a column (10 cm internal diameter, 52 cm height) filled with a molecular sieve. The column packing is composed, for example, of 4 of ®Fractogel TSK HW-40 F (E. Merck, Darmstadt, Germany), a hydrophilic vinyl polymer for the separation, by gel permeation chromatography, of low molecular weight compounds such as dextrans in the molecular weight range of 100–7000 g/mol. A mixture of water and methanol (1:1) containing 1% by volume of added acetic acid is used as the mobile phase. Fractions which contain salmycin B or C are combined and freeze-dried. 510 mg of a crude product are obtained which contains 82% by weight of salmycin B and 3% by weight of salmycin C.

Example 6: Purification of salmycins A and D 1.4 g of crude salmycin A and D are purified, as described in Example 5, using a column filled with a molecular sieve. The mobile phase is composed of four parts of water and one part of ethanol. The fractions which contain salmycin A and D are combined. Concentration and freeze-drying yield 240 mg of a crude product containing 85% by weight of salmycin A and D.

Example 7= Isolation of salmycins A and D in pure form

The material (240 mg) isolated in accordance with Example 6 is dissolved in distilled water and purified by reversed-phase chromatography. A column having an internal diameter of 3.2 cm and a height of 25 cm is packed with 200 ml of $C_{18}$ silica gel, such as, for example, ®Nucleosil 12 $C_{18}$AB (Macherey & Nagel, Düren, Germany). A water/ acetonitrile gradient (0–10% by volume of acetonitrile) is used as the mobile phase. 25 ml fractions are collected. Fractions which contain salmycin D or A are combined.

Concentrating and freeze-drying yield 130 mg of salmycin A (99% by weight) and approximately 1.5 mg of salmycin D.

Characterization of salmycin A:

a) High-resolution FAB mass spectroscopy: Molecular ion peak of M+H$^{+}$:1053.4050±0.0006 daltons. Mass (calculated for M+H$^+$, monoisotopic): 1053.4052 daltons.

Formula: $C_{41}H_{70}FeN_7O_{21}$ b) $^1$H-NMR: Signal at 2.8 ppm in D$_2$O (N-methyl group), no further signals for methyl protons.

c) UV-visible of the aqueous solution (phosphate buffer, pH 7.0):

End absorption and broad absorption around 430 nm (log $\epsilon$= 3.3).

Characterization of salmycin D:

a) ESI MS:

Molecular ion peak of M+H$^+$:1039.8 daltons.

Formula: $C_{40}H_{68}FeN_7O_{21}$ b) UV-visible of the aqueous solution (phosphate buffer, pH 7.0):

End absorption and broad adsorption around 430 nm (log $\epsilon$= 3.3)

Example 8: Isolation of salmycin B and C in pure form

The mixture of salmycin B and C obtained in accordance with Example 5 is purified, as in Example 7, by reversed-phase chromatography. The mobile phase is composed of a mixture of water, 6% by volume of acetonitrile and 0.1% by volume of trifluoroacetic acid. 402 mg of salmycin B and 8 mg of salmycin C are obtained.

Characterization of salmycin B:

a) High-resolution FAB mass spectroscopy:

Molecular ion peak of M+H$^+$:1038.3941±0.0007 daltons

Molecular ion peak of M+H$^+$+H$_2$O:1056.406±0.001 daltons

Mass calculated for M+H$^+$+H$_2$O:1056.4053 daltons

Formula: $C_{41}H_{69}FeN_6O_{21}$ b) $^1$H-NMR: Signal at 2.8 ppm in D$_2$O (N-methyl group), no further signals for methyl protons.

c) UV-visible of the aqueous solution (phosphate buffer, pH 7.0:

End absorption and broad absorption around 427 nm (log $\epsilon$= 3.3).

Characterization of salmycin C:

a) ESI mass spectroscopy (electron spray ionization):

Molecular ion peak of M+H$^+$:1024.4 daltons

Molecular ion peak of M+H$^+$+H$_2$O:1042.4 daltons

Formula: $C_{40}H_{67}FeN_6O_{21}$ b) $^1$H-NMR: Signal at 2.8 ppm in D$_2$O (N-methyl group), no further signals for methyl protons.

c) UV-visible of the aqueous solution (phosphate buffer, pH 7.0):

End absorption and broad absorption around 430 nm (log $\epsilon$= 3.3).

Example 9: Isolation of the potassium salt of desferridanoxamine 100 mg of salmycin A are dissolved in 20 ml of water and the pH is adjusted to pH 9.5 by the dropwise addition of an 0.1 N solution of potassium hydroxide. The hydrolysis is complete after 2 hours. 100 mg of ethylenediaminetetraacetic acid dipotassiumsalt are then added in order to remove the bound iron from the danoxamine which has been formed, and the mixture is left to stand for a further 2 hours. During this period, the solution, which is initially salmon-colored, becomes decolorized. Reversed-phase chromatography is used to separate and purify the desferridanoxamine potassium salt. Use is made of a column, having a height of 25 cm and an internal diameter of 3.2 cm, which is filled with 200 ml of C$_{18}$ silica gel, e.g. ®Nucleosil 12 C$_{18}$ AB (Macherey & Nagel, Düren, Federal Republic of Germany). A mixture of water and acetonitrile with a concentration gradient of 0–15% by volume of acetonitrile is employed as the mobile phase. The product-containing fractions are combined and freeze-dried. 48 mg of a pale-beige powder are obtained. The product has a purity of 98%.

Example 10: Isolation of the sodium salt of desferrinordanoxamine 100 mg of salmycin C are hydrolyzed, in a corresponding manner to Example 9, with an 0.1 N solution of sodium hydroxide, and treated with ethylene-diaminetetraacetic acid disodium salt. Following subsequent purification, 45 mg of desferrinordanoxamine are obtained at a purity of 97%.

Example 11: Isolation of desferrisalmycin A, B, C or D 100 mg of salmycin A, B, C or D are dissolved in phosphate buffer, pH 7. 100 mg of ethylene diamine tetraacetic acid dipotassium salt are then added in order to remove the bound iron, and the mixture is left to stand for 2 hours. During this period, the solution, which is initially salmon-colored, becomes decolorized. Reversed-phase chromatography is used to separate and purify the desferrisalmycin. Use is made of a column, having a height of 25 cm and an internal diameter of 3.2 cm, which is filled with 200 ml of C$_{18}$ silica gel, e.g. ®Nucleosil 12 C$_{18}$ AB (Macherey & Nagel, Düren, Federal Republic of Germany). A mixture of water and acetonitrile with a concentration gradient of 0–15% by volume of acetonitrile is employed as the mobile phase. The product-containing fractions are combined and freeze-dried. A pale-beige powder is obtained. The product is of high purity.

We claim:

1. A compound, termed nordanoxamine, having the empirical formula $C_{26}H_{44}FeN_5O_{11}$ and a molecular weight of 648 g/mol, or an iron-free form thereof, termed desferrinordanoxamine, having the empirical formula $C_{26}H_{47}N_5O_{11}$ and a molecular weight of 605 g/mol; a compound, termed desferrisalmycin A, of the empirical formula $C_{41}H_{73}N_7O_{21}$ and of a molecular weight of 1000 g/mol; a compound, termed desferrisalmycin B, of the empirical formula $C_{41}H_{72}N_6O_{21}$ and of a molecular weight of 985 g/mol; a compound, termed desferrisalmycin C, of the empirical formula $C_{40}H_{70}N_6O_{21}$ and of a molecular weight of 971 g/mol; and a compound, termed desferrisalmycin D, of the empirical formula $C_{40}H_{71}N_7O_{21}$ and of a molecular weight of 986 g/mol.

2. A process for preparing nordanoxamine having the empirical formula $C_{26}H_{44}FeN_5O_{11}$ and a molecular weight of 658 g/mol comprising hydrolyzing salmycin C or D in an alkaline solution.

3. A process for preparing danoxamine having the empirical formula $C_{27}H_{46}FeN_5O_{11}$ and a molecular weight of 672 g/mol comprising hydrolyzing salmycin A, salmycin B or salmycin A and salmycin B in an alkaline solution.

4. A process for preparing desferrinordanoxamine having the empirical formula $C_{27}H_{47}N_5O_{11}$ and a molecular weight of 605 g/mol comprising hydrolyzing salmycin C or D in an alkaline solution and treating the resultant product with g sequestering agent or an iron-binding reagent or by reducing the bound $Fe^{3+}$ ion.

5. A process for preparing desferridanoxamine comprising hydrolyzing salmycin A, salmycin B or salmycin A and B in an alkaline solution and treating the resultant product with a sequestering agent or an iron-binding reagent or by reducing the bound $Fe^{3+}$ iron.

6. A process for preparing desferrisalmycin A of the empirical formula $C_{41}H_{73}N_7O_{21}$ and of a molecular weight of 1000 g/mol, desferrisalmycin B of the empirical formula $C_{41}H_{72}N_6O_{21}$ and of a molecular weight of 985 g/mol, desferrisalmycin C of the empirical formula $C_{40}H_{70}N_6O_{21}$ and of a molecular weight of 971 g/mol and desferrisalmycin D of the empirical formula $C_{40}H_{71}N_7O_{21}$ and of a molecular weight of 986 g/mol comprising treating salmycin A, B, C or D with g sequestering agent or with an iron-binding reagent or by reducing the bound $Fe^{3+}$ ion.

7. A pharmaceutical composition containing one or more compound or a physiologically tolerated salt of one or more compound wherein said compound is selected from the group consisting of desferrinordanoxamine, desferridanoxamine, desferrisalmycin A, desferrisalmycin B, desferrisalmycin C and desferrisalmycin D.

8. A method for the treatment of hemochromatosis or Alzheimer's disease which comprises administering an effective amount of a compound or a physiologically tolerated salt of a compound wherein said compound is selected from the group consisting of desferrinordanoxamine, desferridanoxamine, desferrisalmycin A, desferrisalmycin B, desferrisalmycin C and desferrisalmycin D.

* * * * *

UNITED STATES PATENT AND TRADEMARK OFFICE
CERTIFICATE OF CORRECTION

PATENT NO. : 5,519,123
DATED : May 21, 1996
INVENTOR(S) : László VERTESY et al.

It is certified that error appears in the above-indentified patent and that said Letters Patent is hereby corrected as shown below:

Claim 6, column 10, line 5, "g" should read --a--.

Signed and Sealed this

Nineteenth Day of November, 1996

Attest:

BRUCE LEHMAN

*Attesting Officer*     *Commissioner of Patents and Trademarks*